United States Patent
Linn et al.

(10) Patent No.: US 11,464,760 B2
(45) Date of Patent: Oct. 11, 2022

(54) FRIGOSTABLE COMPOSITION FOR IONTOPHORETIC TRANSDERMAL DELIVERY OF A TRIPTAN COMPOUND

(71) Applicant: LTS Lohmann Therapie-Systeme AG, Andernach (DE)

(72) Inventors: Michael Linn, Waldböckelheim (DE); Christoph Schmitz, Rheinbrohl (DE); Hanshermann Franke, Hamburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 16/772,776

(22) PCT Filed: Dec. 13, 2018

(86) PCT No.: PCT/EP2018/084703
§ 371 (c)(1),
(2) Date: Jun. 13, 2020

(87) PCT Pub. No.: WO2019/121297
PCT Pub. Date: Jun. 27, 2019

(65) Prior Publication Data
US 2020/0330434 A1    Oct. 22, 2020

(30) Foreign Application Priority Data
Dec. 20, 2017 (EP) .................... 17208956

(51) Int. Cl.
*A61K 31/4045* (2006.01)
*A61K 9/00* (2006.01)
*A61K 9/70* (2006.01)
*A61K 31/404* (2006.01)
*A61K 31/422* (2006.01)
*A61K 31/454* (2006.01)
*A61K 47/12* (2006.01)
*A61K 47/32* (2006.01)

(52) U.S. Cl.
CPC ........ *A61K 31/4045* (2013.01); *A61K 9/0014* (2013.01); *A61K 9/7084* (2013.01); *A61K 31/404* (2013.01); *A61K 31/422* (2013.01); *A61K 31/454* (2013.01); *A61K 47/12* (2013.01); *A61K 47/32* (2013.01)

(58) Field of Classification Search
CPC .................................................. A61K 9/7084
See application file for complete search history.

(56) References Cited

U.S. PATENT DOCUMENTS

| | | | |
|---|---|---|---|
| 5,685,837 A | 11/1997 | Horstmann | |
| 6,745,071 B1 | 6/2004 | Anderson et al. | |
| 8,366,600 B2 | 2/2013 | Sebree et al. | |
| 2009/0318847 A1* | 12/2009 | Sebree | A61N 1/30 604/20 |

FOREIGN PATENT DOCUMENTS

| | | |
|---|---|---|
| EP | 1 253 913 A1 | 11/2002 |
| EP | 2 285 362 A1 | 2/2011 |
| WO | 2008/140453 A1 | 11/2008 |
| WO | 2009/154648 A1 | 12/2009 |
| WO | 2009/154649 A1 | 12/2009 |
| WO | 2011/046927 A1 | 4/2011 |
| WO | WO-2018006069 A1 * | 1/2018 ......... A61K 31/4045 |

OTHER PUBLICATIONS

U.S. Pat. No. 222,276, Hunter, dated Dec. 2, 1879 (fillable form will not allow six digit patent number).
U.S. Pat. No. 486,902, Shults, dated Nov. 29, 1892.
Siegel, Steven J., et al., "A Unique Iontophoretic Patch for Optimal Transdermal Delivery of Sumatriptan," Pharmaceutical Research, vol. 24, No. 10, Jun. 19, 2007, pp. 1919-1926.
International Search Report of PCT/EP2018/084703, International Filing Date Dec. 13, 2018.
International Preliminary Report on Patentability, PCT/EP2018/084703.

* cited by examiner

*Primary Examiner* — Mark V Stevens
*Assistant Examiner* — Alparslan Asan
(74) *Attorney, Agent, or Firm* — ProPat, LLC; Cathy R. Moore; Vinisha Joshi

(57) ABSTRACT

The present invention relates to frigostable compositions suitable for iontophoretic transdermal delivery of a triptan compound that includes: a salt of a triptan compound, preferably sumatriptan succinate, a polyamine, one or more dicarboxylic acids, 0.5 to 10.0 wt.-% (based on the total weight of the composition) of one or more monocarboxylic acids, and water or an aqueous solvent mixture. The invention further relates to the use of the composition as an integral component of an iontophoretic patch, preferably as an anodic reservoir of the patch.

14 Claims, 2 Drawing Sheets

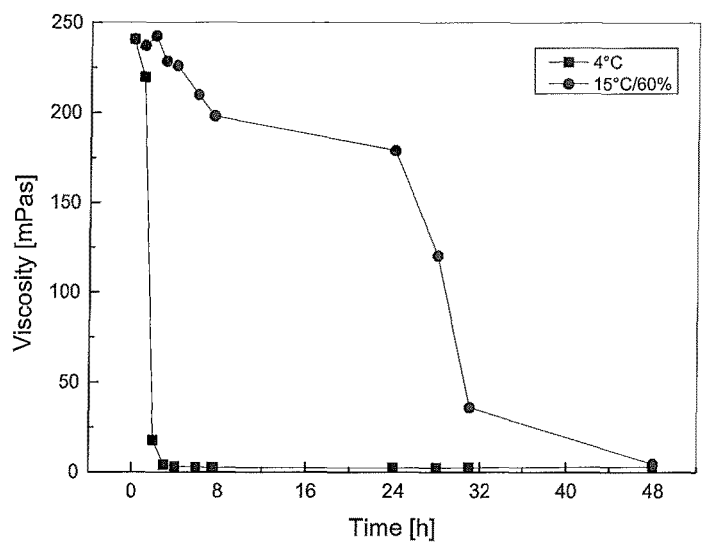
Figure 1: Frigostability of Comparative Example (US-A 8,366,600 paragraph [0063])
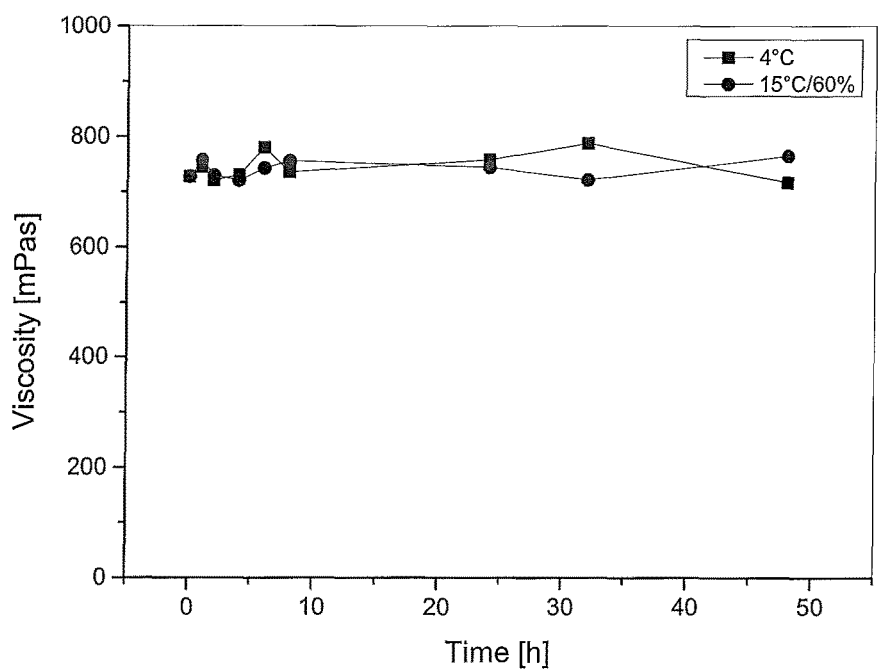
Figure 2: Frigostability of Example 3

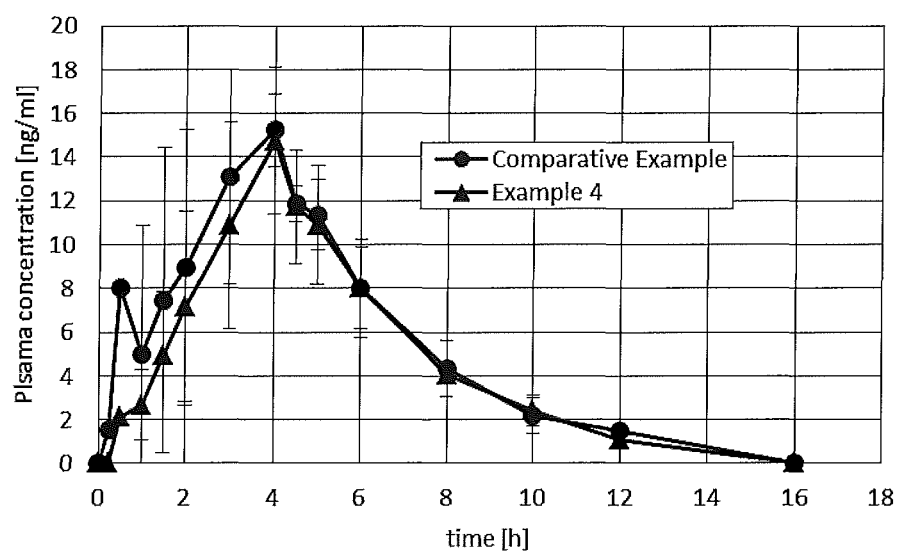
Figure 3: Time dependent plasma concentration of the Comparative Example and Example 4

FRIGOSTABLE COMPOSITION FOR IONTOPHORETIC TRANSDERMAL DELIVERY OF A TRIPTAN COMPOUND

CROSS-REFERENCE TO RELATED APPLICATIONS

This application is being filed under 35 U.S.C. § 371 as a National Stage Application of International Application No. PCT/EP2018/084703 filed Dec. 13, 2018, which claims priority to the following parent application: European Patent Application No. 17208956.7, filed Dec. 20, 2017. Both International Application No. PCT/EP2018/084703 and European Patent Application No. 17208956.7 are hereby incorporated by reference herein in their entirety.

FIELD OF INVENTION

The present invention relates to frigostable compositions suitable for iontophoretic transdermal delivery of a triptan compound, preferably Sumatriptan.

BACKGROUND ART

The transdermal route of parenteral administration provides many advantages over other routes of administration. Methods and devices for administering drugs through the skin are well known in the field of pharmaceuticals. Typically, transdermal administration is effected by using passive transdermal systems (e.g. Transdermal Therapeutic Systems, TTS) which deliver drug substances through the skin at defined rates by diffusion processes. Therefore, transdermal drug delivery is very inefficient for certain types of drug substances. In particular, ionized drugs are often unable to passively permeate through the skin at therapeutically effective rates.

The process of iontophoresis was originally described by LeDuc in 1908, and even earlier in U.S. Pat. No. 222,276 (1879) and U.S. Pat. No. 486,902 (1892). Since then, iontophoresis has found commercial use in the delivery of ionically charged therapeutic drug molecules such as pilocarpine, lidocaine, dexamethasone and fentanyl.

Generally, iontophoresis is a delivery method which relies on the basic principle that application of electric current can provide external energy to enable or enhance the passage of drug ions across the skin, presumably by increasing drug permeability through the membranes of the skin. When ions bearing a positive charge (e.g. cationic active agents) are placed into or under the anode of an iontophoretic system, these ions will then—upon application of current—be forced to move away from the anode and, following the direction of the electrical field, towards the cathode which is placed on an adjacent skin area. During this process, transport of the cationic drug through the skin is enhanced or facilitated. Iontophoresis may be used with different forms of active pharmaceutical ingredients, most favorably with those carrying an electrical charge, which are thus directly moved across barriers (e.g. the skin) within an electrical field.

In iontophoresis, different to diffusion-controlled transdermal delivery described above, the skin contact area of the device and the active ingredient concentration within the device are less important with respect to the level of skin flux of the active ingredient. The delivery of active ingredient through the skin is largely dependent on the applied current by which the active ingredient can be forced into the skin.

A typical iontophoretic drug delivery system includes an electrolytic electrical system comprising an anode and a cathode to be adhered to different—preferably adjacent—skin areas of a patient, each electrode being connected by a wire to a remote power supply, generally a microprocessor-controlled electrical instrument. Such types of devices have been published, including systems with a lean construction (e.g. U.S. Pat. Nos. 5,685,837 or 6,745,071) as well as more sophisticated systems, which systems are basically known to the expert. Iontophoretic transdermal systems for lidocaine and fentanyl are introduced into the US market.

Transdermal drug transport by iontophoresis is a complex process which may be affected by a variety of parameters, such as the concentration of electrolytes, ionic strength, the type, composition and viscosity of the electrode material, the duration of iontophoresis, skin resistance, or area size of the electrodes. In general, little is known about the various influences of these parameters on the iontophoretic process.

Furthermore, in order to meet the strict galenic requirements, transdermal iontophoretic devices must contain defined electrolyte concentrations having defined ionic strengths, in order to ensure that the active substance is transported into the skin at a desired and constant rate, and to ensure that the transdermally administered dose is both safe and therapeutically effective.

EP-A 2 285 362 describes compositions for transdermal iontophoretic devices wherein the compositions comprise a polyamine or polyamine salt, e.g. EUDRAGIT® E 100 which accounts for the above galenic requirements.

The "ZECUITY®-Patch" (TEVA Pharmaceuticals Industries, Ltd.), a sumatriptan iontophoretic transdermal system for the acute treatment of migraine also seems to fulfill the above galenic requirements. However, this sumatriptan composition is instable at low temperatures. It requires storage and shipping conditions of 15° C. or higher. Exposition of the sumatriptan composition to temperatures of lower than 15° C. leads to an irreversible liquefaction (loss of viscosity, "leaking" patch) of the composition and a precipitation of lauric acid.

In view of the above, it is therefore one major object of the present invention to provide a triptan composition, preferably a Sumatriptan composition that is stable at low temperatures, specifically at temperatures at or below 15° C. (frigostability). Specifically it is an object to avoid a precipitation of crystals and to maintain or even increase the viscosity of the triptan composition compared to the original ZECUITY® formulation.

SUMMARY OF THE INVENTION

In view of the above object, the present invention provides improved compositions for iontophoretic transdermal delivery of a triptan compound, preferably sumatriptan.

The sumatriptan iontophoretic transdermal composition according to U.S. Pat. No. 8,366,600 which suffers from the above described disadvantages comprises:
approximately 3.0% to about 5.0% sumatriptan succinate;
approximately 84% to about 88% water;
approximately 4.0% to about 7.0% alkylated methacrylate co-polymer;
approximately 1.0% to about 6.0% fatty acids (e.g., about 1.0% to about 5.0% lauric acid and about approximately 0.05% to about 0.75% adipic acid); and
approximately 0.05% to about 0.75% methyl para-hydroxy benzoate.

The composition according to U.S. Pat. No. 8,366,600 (which is hereby incorporated by reference herein) exhibits an equimolar ratio between the basic groups of the polyamine (alkylated methacrylate co-polymer) and the acid functions of lauric acid and adipic acid (calculated with a valence of 1) so as to neutralize the pH value of the composition.

In the present invention the amount of polyamine is increased in the formulation and the necessary neutralization of the polyamine, preferably EUDRAGIT® E 100, is performed by an increased amount of organic acid(s), specifically an increased amount of dicarboxylic acids, e.g. adipic acid and/or succinic acid. The viscosity necessary for use in a TTS can be achieved by increasing the solids content of the solution. This variation in the amount of polyamine and dicarboxylic acid surprisingly improved the frigostability of the triptan composition.

The preferred polyamine EUDRAGIT® E 100 is made from three different methacrylate-monomers: dimethylaminoethylmethacrylate, butylmethacrylate and methylmethacrylate in a ratio of about 2:1:1. EUDRAGIT® E 100, has basic functions. These basic functions, which appear protonated (polycationic) at the present pH, provide sufficient conductivity of the composition for iontophoretic transdermal application thereof. The compositions have a higher conductivity than the composition according to U.S. Pat. No. 8,366,600, which is an advantage, since a lower voltage can be used for achieving the desired current flow.

The viscosity of the mass can be arbitrarily adjusted by adjusting the solids content of the solution. Thus, the mass for dosing and transfer into the pad can be optimized. In this way, a potential leakage of the commercial patches (due to the viscosity reduction) can be minimized; frigostability is, thus, improved.

Therefore, the invention pertains to a composition for iontophoretic transdermal delivery of a salt of a triptan compound, comprising:
  a salt of a triptan compound, preferably a succinate
  a polyamine
  a dicarboxylic acid
  a monocarboxylic acid
  water or an aqueous solvent mixture; and
  optionally, one or more additives.

In a further embodiment, the composition comprises between 10.0 and 60.0 wt.-% of one or more alkylated methacrylate polyamine copolymer(s), between 0.5 and 10 wt.-% of a salt of a triptan compound, preferably sumatriptan, between 1.0 and 10.0 wt.-% of one or more dicarboxylic acid(s), between 1.0 and 10.0 wt.-% of a monocarboxylic acid, optionally one or more additives and water.

The invention further encompasses the use of said composition as a component for an iontophoretic transdermal patch.

The invention further encompasses the use of said composition in a method for the iontophoretic transdermal administration of a triptan compound, preferably sumatriptan to subjects requiring treatment with a triptan compound.

BRIEF DESCRIPTION OF THE FIGURES

FIG. 1 is a graphical illustration of the frigostability of the Comparative Example (U.S. Pat. No. 8,366,600 paragraph [0063]);

FIG. 2 is a graphical illustration of the frigostability of Example 3; and

FIG. 3 is a graphical illustration of the time dependent plasma concentration of the Comparative Example and Example 4.

DETAILED DESCRIPTION

The compositions according to the present invention comprise water or an aqueous solvent mixture. Preferably, the proportion of water or solvent mixture is at least 30 wt.-%, more preferably 40 wt.-%, relative to the total weight of the composition. According to a further embodiment, the water content or the proportion of said solvent mixture is in the range of 40 to 80 wt.-%.

The term "aqueous solvent mixture" generally includes liquid mixtures containing water and at least one further solvent which is generally selected from polar, water-miscible solvents such as, for instance, alcohols (e.g. ethanol, isopropanol, glycerol).

According to a preferred embodiment of the invention, the polyamine is EUDRAGIT® E 100, which is made from three different methacrylate-monomers: dimethylaminoethyl-methacrylate, butylmethacrylate and methylmethacrylate in a ratio of about 2:1:1.

Preferably, the proportion of polyamine is between 10.0 and 30.0 wt.-%, preferably between 15.0 and 25.0 wt.-% (based on the total weight of the composition).

In further embodiments of the present invention, the composition further comprises at least one dicarboxylic acid and at least one monocarboxylic acid. Specifically the amount of dicarboxylic acid(s) is increased compared to the composition according to U.S. Pat. No. 8,366,600 for triptan compositions for iontophoretic devices. It has been found that an increased amount of polyamine together with an increased amount of organic acid(s), specifically an increased amount of dicarboxylic acids, e.g. adipic acid and/or succinic acid improves the frigostability of the composition.

By combining the above-discussed polyamine with one or more dicarboxylic acid(s), and one or more monocarboxylic acid(s), corresponding polyamine salts are obtained. These polyamine salts are generally water-soluble and, upon dissolution in water, form a polymeric electrolyte. The present compositions comprising said polyamine salts are particularly suitable as a carrier or reservoir for triptans, preferably sumatriptan in iontophoretic devices.

The term "dicarboxylic acid" generally includes organic compounds that are substituted with two carboxylic acid functional groups, which compounds include linear, branched and cyclic compounds, which compounds may be saturated or unsaturated. For instance, the dicarboxylic acid may be selected from $C_4$ to $C_{10}$ dicarboxylic acids. Examples of dicarboxylic acids include succinic acid, glutaric acid, adipic acid and pimelic acid; succinic acid and adipic acid being preferred.

In further embodiments, the composition may contain a combination comprising at least two dicarboxylic acids.

Preferably, the total amount of dicarboxylic acid(s) in the composition is between 0.5 and 10.0 wt.-%, preferably between 1.0 and 5.0 wt.-% (based on the total weight of the composition).

The term "monocarboxylic acid" generally includes organic compounds that are substituted with one carboxylic acid functional group, which compounds include linear, branched and cyclic compounds, which compounds may be saturated or unsaturated. For instance, the monocarboxylic acid may be selected from $C_6$ to $C_{22}$ monocarboxylic acids. Examples of monocarboxylic acids include saturated acids like capric acid, lauric acid, myristic acid, palmitic acid, stearic acid and arachidic acid or those containing double bonds like myristoleic acid, palmitoleic acid, oleic acid, and linoleic acid; lauric acid being preferred.

In further embodiments, the composition may contain a combination comprising at least two monocarboxylic acids.

Preferably, the total amount of monocarboxylic acid(s) in the composition is between 0.5 and 5.0 wt.-%, preferably between 2.0 and 4.0 wt.-% (based on the total weight of the composition).

Generally, the amount of monocarboxylic acid(s) and dicarboxylic acid(s) is adjusted so as to be at least sufficient to solubilize the polyamine(s), and/or other components present in said composition, in order to obtain a hydrogel composition having the desired properties, particularly semisolid consistency as well as skin-adhesive properties.

The ratio of basic functions (from the polyamine) to free acid functions, e.g. from lauric, adipic, succinic acid etc., is preferably 1.25 or larger, more preferably 1.28 or larger and most preferably 1.30 or larger. This ratio is calculated as follows:

(Amount of acid [grams]÷ molecular weight)× valence=mols Acid (the valence of adipic acid and succinic acid is 2, except for the corresponding amount of succinic acid which is bound to sumatriptan for which the valence is 1; the valence of lauric acid is 1).

Polyamine:

Amount of Polyamine [grams]×0.18=Alkali-number for EUDRAGIT®, acc. Manufacturers specification)=grams KOH (equivalent for the base).

grams KOH/56.11 (=molecular weight of KOH)=mols Base

Base/Acid-Ratio:

The ratio of "mols Base" to "mols Acid" is the Base/Acid Ratio.

The term "triptan compound" includes triptan compounds, derivatives and salts. The term also includes compounds that contain a 2-(1H-indol-3-yl)-N,N-dimethyl-ethanamine moiety. Examples of triptan compounds include, but are not limited to, almotriptan, frovatriptan, eletriptan, zolmitriptan, rizatriptan, sumatriptan, naratriptan, and pharmaceutically acceptable salts thereof. The preferred triptan is sumatriptan and the preferred salt is a succinate.

As described above, the compositions of the present invention are formulated as aqueous compositions, particularly as hydrogel compositions. In a further embodiment, the said aqueous compositions have a pH of 3 to 8, preferably 4.0 to 6.0, or most preferably 4.3 to 5.8.

Generally, it is preferred to adjust and maintain the pH in said water-containing compositions so that they do not substantially affect the pH of the skin, when the compositions are applied to the skin (e.g. during transdermal or iontophoretic administration).

The composition according to the present invention may optionally contain one or more further additives. Said additives include, but are not limited to, additives selected from the group comprising solubility enhancers, skin permeation enhancers, preservatives and antimicrobial agents.

In this connection, the term "solubility enhancer" generally relates to compounds capable of increasing the solubility of the cationic active agent within the composition. This can be achieved either by modulating the possible interactions between said cationic active agent and the other components present in the composition, or by additionally incorporating suitable excipients.

Alternatively, the solubility of the active agent can be achieved by changing its crystal modification. Examples of solubility enhancers include, without limitation, water; diols such as propylene glycol and glycerol; monoalcohols such as ethanol, propanol and higher alcohols; dimethylsulfoxide (DMSO), dimethylformamide, N,N-dimethylacetamide, N-substituted alkyl-azacycloalkyl-2-ones. As already described above, compounds selected from the group of dicarboxylic acids are particularly effective for enhancing the solubility of the polyamine(s).

Further, the term "skin permeation enhancer" particularly includes compounds capable of increasing the permeability of the skin for an active agent contained in the composition, particularly for a cationic active agent. Due to this increase in skin permeability, the rate at which the active agent(s) permeate(s) through the skin and enter(s) the blood circulation is also increased. The enhanced permeation effected by the use of said skin permeation enhancers can be assayed and confirmed by measuring the rate of active agent diffusion through animal or human skin using a diffusion cell apparatus generally known in the art.

Examples of permeation enhancers include, but are not limited to, dimethylsulfoxide (DMSO), N,N-dimethylacetamide (DMA), decylmethylsulfoxide (C10 MSO), polyethylene glycol monolaurate (PEGML), propylene glycol (PG), propylene glycol monolaurate (PGML), glycerol monolaurate (GML), lecithin, the 1-substituted alkyl-azacycloalkyl-2-ones, particularly 1-n-dodecylazacycloheptan-2-one, alcohols, and the like. The permeation enhancer may also be selected from vegetable oils, e.g. safflower oil, cotton seed oil, or corn oil. Combinations comprising two or more different permeation enhancers may also be used.

Further, the term "antimicrobial agent" generally includes agents which are capable of preventing the growth of microbes in a pharmaceutical preparation, particularly in a composition according to the present invention. Examples of suitable antimicrobials include, but are not limited to, salts of chlorhexidine, such as iodopropynyl butylcar-bamate, diazolidinyl urea, chlorhexidine digluconate, chlorhexidine acetate, chlorhexidine isethionate, chlorhexidine hydrochloride. Other cationic antimicrobial agents may also be used, such as benzalkonium chloride, benzethonium chloride, triclocarbon, polyhexamethylene biguanide, cetylpyridinium chloride, methylbenzethonium chloride.

Other antimicrobial agents include, but are not limited to, halogenated phenolic compounds, such as 2,4,4'-trichloro-2-hydroxy diphenyl ether (Triclosan), parachlorometa xylenol (PCMX); methyl para-hydroxybenzoate; and short-chain alcohols such as ethanol, propanol, and the like. Preferably, the total concentration of said antimicrobial agent(s) is in the range of 0.01 to 2 wt.-%, relative to the total weight of the composition in which it is included.

In further embodiments, the composition may comprise between 0.01 and 1.0 wt.-%, preferably between 0.09 and 0.2 wt.-%, more preferably about 0.10 of methyl parahydroxybenzoate (NIPAGIN™).

According to a further embodiment, the composition of the present invention has adhesive properties, to ensure that the composition is maintained in direct and complete contact with the skin at the site of application during the whole time period of transdermal drug administration. Adhesiveness can be obtained by incorporating one or more adhesive polymers into said compositions. Adhesive polymers suitable for this purpose are generally known to the skilled person. Preferably, a polyamine or polyamine salt having adhesive properties is used as said adhesive polymer(s).

Preferably, the compositions of the present invention are self-adhesive. To render the compositions self-adhesive, they may further contain one or more additives selected from the group of tackifiers which group includes, but is not limited to, hydrocarbon resins, rosin derivatives, glycols (such as glycerol, 1,3-butanediol, propylene glycol, polyethylene glycol).

The present invention further pertains to any embodiments of the present invention that may result from combining two or more of the above-described embodiments, or from combining one or more individual features that are mentioned throughout the above description with any one of the above-described embodiments of the present invention.

Generally, the compositions of the present invention can be manufactured by conventional methods. Broadly, the compositions of the present invention are obtainable by dissolving or dispersing the various ingredients (i.e. triptan, polyamine, acids, additives) in water or an aqueous solvent mixture. The resulting mixture may then be spread on a flat surface or poured into molds or extruded, and then allowed to solidify to obtain hydrogel compositions having the desired shape.

The present invention further encompasses the use of the above-described composition(s) as an integral component of an iontophoretic patch, preferably as an anodic reservoir of the patch. Preferably, such composition is incorporated into said iontophoretic patch during manufacture, to form the anodic reservoir of the patch. The above-mentioned administration forms are obtainable by manufacturing methods generally known in the art. EP-A 2 285 362 (whose United States equivalent US 2011/0111029 A1 is hereby incorporated by reference herein) shows how the above composition(s) may be included in an iontophoretic device.

The methods further include iontophoretic methods for transdermal administration. Generally, the above-mentioned methods comprise a step of applying a composition according to the present invention to the skin of said subject, and allowing the active agent e.g. sumatriptan contained in the composition to be released therefrom and to permeate through the skin and to enter the blood circulation of said subject. This process is enhanced by iontophoresis.

EXAMPLES

In the following, the invention and its effectiveness are illustrated by means of examples, together with the attached drawing.

FIG. 1 shows the viscosity degradation over time of the composition according to U.S. Pat. No. 8,366,600 at 4° C. and 15° C.

Methods

Conductivity measurements were performed by a VWR EC 300 conductometer.

The pH was measured by a Seven Compact pH/ion meter S220.

Viscosity measurements were performed by a Thermo Scientific HAAKE™ RHEOSTRESS™ 6000 rheometer.

Experimental Procedure

The compositions were prepared with a standard laboratory equipment (stirrer, water bath, glassware). The compositions were prepared as follows:
1. Reactor vessel was filled with water
2. methyl para-hydroxy benzoate (NIPAGIN™) was added under continuous stirring
3. Premix of EUDRAGIT® E100, lauric acid and adipic acid added into the vessel
4. The solution was heated to 80° C. for 2 h while continuous stirring
5. Solution was cooled down to 25° C.

The final composition and the measured key parameters are summarized in Tables 1 (composition according to U.S. Pat. No. 8,366,600) and 2 (compositions with increased amount of EUDRAGIT® E 100 and adipic acid).

TABLE 1

Composition and parameters of the composition according to U.S. Pat. No. 8,366,600
Comparative Example (U.S. Pat. No. 8,366,600 paragraph [0063])

| Raw material | Amount |
| --- | --- |
| Sumatriptan succinate | 4.00% |
| Lauric acid | 3.40% |
| Adipic acid | 0.27% |
| EUDRAGIT ® E 100 | 5.86% |
| Nipagin ™ | 0.10% |
| Aqua purificata | 86.37% |
| Conductivity | 4.03 mS/cm |
| pH | 5.2 |
| Viscosity | 221 mPas |
| Base/Acid Ratio | 0.66 |
| Frigostability * | — |

* see explanation under table 2

Frigostable compositions with increased amount of EUDRAGIT® E 100 and adipic acid (Examples 1-7)

The frigostable compositions were obtained by increasing the amount of adipic acid and EUDRAGIT® E 100. The resulting formulation and its key parameters are shown in Table 2.

TABLE 2

Frigostable compositions with EUDRAGIT ® E 100 and adipic acid and lauric acid

| Raw material | Example 1 | Example 2 | Example 3 | Example 4 | Example 5 | Example 6 | Example 7 |
| --- | --- | --- | --- | --- | --- | --- | --- |
| Sumatriptan succinate | 4.00% | 4.00% | 4.00% | 4.00% | 4.00% | 4.00% | 4.00% |
| Adipic acid | 2.78% | 2.64% | 2.59% | 2.53% | 2.48% | 2.43% | 2.53% |
| Lauric acid | 3.82% | 3.63% | 3.55% | 3.48% | 3.41% | 3.34% | 3.48% |
| EUDRAGIT ® E 100 | 19.08% | 18.13% | 17.74% | 17.39% | 17.03% | 16.68% | 18.00% |
| Aqua purificata | 70.22% | 71.50% | 72.02% | 72.50% | 72.97% | 73.45% | 71.89% |
| NIPAGIN ™ | 0.10% | 0.10% | 0.10% | 0.10% | 0.10% | 0.10% | 0.10% |
| Solids content [%] | 29.78 | 28.50 | 27.98 | 27.50 | 27.03 | 26.55 | 28.11% |
| Conductivity [mS/cm] | 5.72 | | 5.78 | 5.78 | | | 5.95 |
| pH | 5.74 | | 5.69 | 5.81 | | | 5.73 |
| Viscosity [mPas] | 2331 | 1236 | 809.9 | 510 | 396.4 | 303.6 | 828.5 |

TABLE 2-continued

Frigostable compositions with EUDRAGIT ® E 100 and adipic acid and lauric acid

| Raw material | Example 1 | Example 2 | Example 3 | Example 4 | Example 5 | Example 6 | Example 7 |
|---|---|---|---|---|---|---|---|
| Base/Acid Ratio | 1.28 | 1.27 | 1.26 | 1.25 | 1.25 | 1.24 | >1.30 |
| Frigostability * | ++ | ++ | ++ | + | + | + | +++ |

\* − bad (irreversible precipitation after 3 days or less at 4° C.; reduced viscosity)
+ good (reversible precipitation after 3 days at 4° C.; stable viscosity)
++ very good (very little reversible precipitation, very small crystals after several weeks at 4° C.; stable viscosity)
+++ excellent (no precipitation after several weeks at 4° C.; stable viscosity)

The frigostability of Example 3 is shown in FIG. 2.

Preclinical Study

A preclinical study has been performed in 3 female Gottingen SPF minipigs per formulation by use of the compositions according to the Comparative Example of U.S. Pat. No. 8,366,600 paragraph [0063](see table 1) and according to Example 4 of the present invention (see table 2). Two iontophoretic transdermal patches containing the same formulation (one activated and one inactivated) were placed dermally on each animal for a period of 4 hours. All drug pads in the patches contained 104 mg sumatriptane succinate. The exposure period has been 4 hours. Blood sampling was performed at the following time points: pre-treatment, and 15 min, 30 min, 60 min, 90 min, 2, 3, 4, 4.5, 5, 6, 8, 10, 12 and 16 hours post-treatment. Concentrations of sumatriptane in plasma samples were determined using solid phase extraction for sample preparation, followed by LC-MS/MS. The results of the study are shown in FIG. 3.

FIG. 3 shows the time dependent plasma concentration of sumatriptane using the compositions according to the Comparative Example and according to Example 4.

The invention claimed is:

1. A composition for iontophoretic transdermal delivery of a salt of a triptan compound, comprising:
    a salt of a triptan compound,
    a polyamine comprising dimethylaminoethyl-methacrylate, butylmethacrylate and methylmethacrylate, said polyamine comprising dimethylaminoethyl-methacrylate, butylmethacrylate and methylmethacrylate present in a minimum amount of 15 wt %,
    one or more dicarboxylic acid, present in an amount ranging from greater than 1.0% to 10.0 wt.-%,
    0.5 to 10.0 wt.-% (based on the total weight of the composition) of one or more monocarboxylic acids,
    water or an aqueous solvent mixture,
    wherein the one or more dicarboxylic acids are selected from the group consisting of succinic acid, glutaric acid, adipic acid and pimelic acid,
    wherein the one or more monocarboxylic acids are selected from capric acid, lauric acid, myristic acid, palmitic acid, stearic acid, arachidic acid, myristoleic acid, palmitoleic acid, oleic acid, and linoleic acid,
    wherein said composition has a pH ranging from 3 to 8, and
    wherein the molar ratio of the base functionalities to acid functionalities of the composition is greater than 1.25.

2. The composition according to claim 1, wherein the triptan compound is a compound that contains a 2-(1H-indol-3-yl)-N,N-dimethylethanamine moiety.

3. The composition according to claim 2, wherein the triptan compound is almotriptan, frovatriptan, eletriptan, zolmitriptan, rizatriptan, sumatriptan or naratriptan.

4. The composition according to claim 1, wherein the salt is a succinate.

5. The composition according to claim 1, further comprising one or more additives.

6. An iontophoretic patch comprising the composition of claim 1 as an integral component.

7. A method of iontophoretic transdermal administration of a triptan compound comprising a step of applying the composition according to claim 1 to a subject's skin, and allowing the triptan compound contained in the composition to be released therefrom and to permeate through the skin facilitated by iontophoresis and to enter the blood circulation of said subject.

8. The composition according to claim 3, wherein the triptan compound is sumatriptan.

9. The composition according to claim 1, wherein the one or more dicarboxylic acids are selected from the group consisting of succinic acid and adipic acid.

10. An iontophoretic patch according to claim 6 comprising the composition of claim 1 as an anodic reservoir of the patch.

11. The composition according to claim 1, wherein the dicarboxylic acids and monocarboxylic acids are present in a total amount ranging from 6.01 to 6.6 wt %.

12. A composition for iontophoretic transdermal delivery of a salt of a triptan compound, comprising:
    a salt of a triptan compound,
    from 15 to 30% of a polyamine comprising dimethylaminoethyl-methacrylate, butylmethacrylate and methylmethacrylate,
    one or more dicarboxylic acids,
    one or more monocarboxylic acids, and
    water or an aqueous solvent mixture,
    wherein the dicarboxylic acid is adipic acid, present in an amount ranging from greater than 1.0% to 10.0 wt.-%,
    wherein the one or more monocarboxylic acids are selected from capric acid, lauric acid, myristic acid, palmitic acid, stearic acid, arachidic acid, myristoleic acid, palmitoleic acid, oleic acid, and linoleic acid,
    said composition has a pH ranging from 4.3 to 8, and
    wherein the molar ratio of the base functionalities to acid functionalities of the composition is greater than 1.25.

13. The composition according to claim 12, wherein the composition exhibits a conductivity ranging from 5.72 to 5.95 mS/cm.

14. The composition according to claim 12, wherein the composition exhibits a viscosity ranging from 303.6 to 2331 mPas.

\* \* \* \* \*